(12) United States Patent
Morris, Jr. et al.

(10) Patent No.: US 6,387,923 B2
(45) Date of Patent: May 14, 2002

(54) IMMINORIBITOL PNP INHIBITORS, PREPARATION THEREOF AND USE THEREOF

(75) Inventors: Philip E. Morris, Jr.; John A. Montgomery; Yarlagadda S. Babu, all of Birmingham, AL (US)

(73) Assignee: Biocryst Pharmacueticals, Inc., Birmingham, AL (US)

( * ) Notice: Subject to any disclaimer, the term of this patent is extended or adjusted under 35 U.S.C. 154(b) by 0 days.

(21) Appl. No.: 09/813,832

(22) Filed: Mar. 22, 2001

Related U.S. Application Data

(60) Provisional application No. 60/191,091, filed on Mar. 22, 2000.
(51) Int. Cl.[7] ................... A61K 31/437; A61K 31/404; C07D 401/04; C07D 471/04; A61P 35/00
(52) U.S. Cl. ................ 514/300; 514/414; 514/44; 546/113; 548/466; 536/4.1; 536/23.1; 536/25.3
(58) Field of Search ................ 514/300, 414; 546/113; 548/466

(56) References Cited

U.S. PATENT DOCUMENTS 5,985,848 A * 11/1999 Furneaux ............... 514/44

* cited by examiner

*Primary Examiner*—Evelyn Mei Huang
(74) *Attorney, Agent, or Firm*—Connolly Bove Lodge & Hutz LLP

(57) ABSTRACT

Compounds represented by the formula:

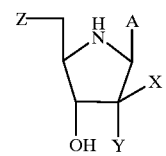

wherein A is selected from the group consisting of

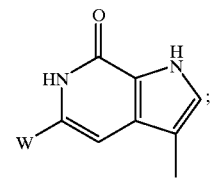

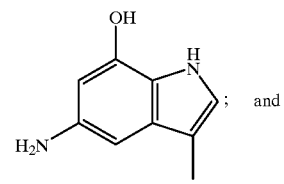

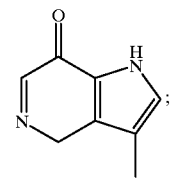

W is $NH_2$ or H; and each X, Y and Z is individually selected from the group consisting of OH, H and halogen provided at least one of X and Y is H; tautomers, or pharmaceutically acceptable salts thereof; are provided. Compounds of the present invention are useful as inhibitors of PNP and of T-cell proliferation. Compounds of the present invention are useful for treating Cancer. Method for preparing the compounds of the present invention are also provided.

5 Claims, No Drawings

IMMINORIBITOL PNP INHIBITORS, PREPARATION THEREOF AND USE THEREOF

CROSS REFERENCES TO RELATED APPLICATION

The present application claims priority under 35 USC 119(e) from U.S. Provisional Application No. 60/191,091 filed Mar. 22, 2000, and entitled "Imminoribitol PNP Inhibitors, Preparation Thereof and Use Thereof."

TECHNICAL FIELD

The present invention relates to certain deaza ring compounds. Compounds of the present invention are especially suitable as inhibitors of purine nucleoside phosphorylase (PNP). The present invention also relates to pharmaceutical compositions comprising the composition of the present invention, as well as methods of using the compounds in inhibiting PNP and in inhibiting T-cell proliferation in a mammal. The present invention also relates to treating cancer in a mammal.

The present invention also relates to a method for producing the compounds of the present invention.

BACKGROUND OF INVENTION

The enzyme purine nucleoside phosphorylase (PNP) catalyses the reversible cleavage of purine nucleosides to the purine base and ribose-1-phosphate. Several cases of a rare genetic disorder in which PNP is lacking have been reported in children. These children are found to be T-cell immunodeficient while their B-cell immunity remained normal. This observation helped establish the relationship between PNP and T-cells and provided the impetus for the development of inhibitors of PNP which may be useful for the treatment of T-cell proliferative disorders. PNP functions as a salvage enzyme in the purine pathway. It is responsible for the reversible phosphorolysis of the ribonucleotides and 2'-deoxyribonucleotides of guanine, hypoxanthine, and related nucleotides to the free base and the phosphorylated sugar. Within intact cells, PNP normally acts in the phosphorolytic direction since the 6-oxopurines are further metabolized.

In children with enzyme deficiency, there is a low uric acid concentration since hypoxanthine and guanine catabolism is shut off and there are high inosine, guanosine, 2'-deoxyinosine, and dGuo nucleoside levels in plasma and urine. From the elevated nucleoside pool, only the elevated levels of dGuo have an inhibitory effect on T-cells. The elevated levels and dGuo become rapidly phosphorylated within these cells to 2'-deoxyguanosine monophosphate (dGMP) by their high level of 2'-deoxycytidine kinase (dCK). dGMP is further phosphorylated to its triphosphate (dGTP), which, in turn, shuts off DNA synthesis, preventing T-cell proliferation and eventually resulting in cell death. Only proliferating T-cells are impaired by this mechanism.

Accordingly, it would be desirable to develop a potent PNP inhibitor.

SUMMARY OF INVENTION

The present invention relates to certain pyrrolidine compounds and particularly to compounds represented by the following formula:

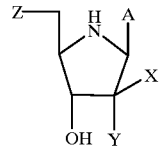

wherein A is selected from the group consisting of

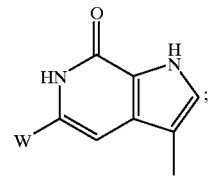

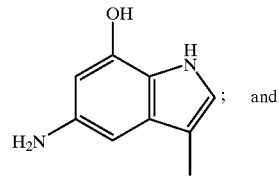

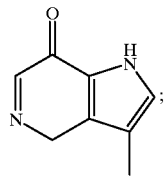

W is $NH_2$ or H; each X, Y and Z independently is selected from the groups consisting of HOH and halogen provided that at least one of X and Y is H; tautomers, and pharmaceutically acceptable salts thereof.

Another aspect of the present invention relates to pharmaceutical compositions containing at least one of the above-disclosed compounds.

The present invention also relates to a method for suppressing purine nucleoside phosphorylase in a patient by administering to the patient at least one of the above-disclosed compounds in an amount sufficient to suppress purine nucleoside phosphorylase.

A still further aspect of the present invention relates to suppressing T-cell proliferation by administering to a patient at least one of the above-disclosed compounds in an amount sufficient to suppress T-cell proliferation.

The present invention is also concerned with methods of using the compounds of the present invention in treating cancer is a mammal.

Still further aspects of the present invention are concerned with preparing the above-disclosed compounds. In particular, compounds wherein A is represented by formula 1 above can be prepared as follows:

1. Converting 3,9-dideaza hypoxanthine (7) to the corresponding 6-chloro compound;
2. Protecting the NH group with a blocking compound;
3. Replacing the 6-chloro group with an alkoxy group;
4. Brominating the compound from step 3 to provide the corresponding bromo compound;
5. Reacting the compound from step 4 with an alkyl lithium compound to replace the bromo group with a lithium group; or forming a Grignard of the bromo compound from step 4;

6. Condensing the compound from step 5 with 5-O-t-butyldimethyl-silyl-1, N-dehydro-1,4-dioxy, 1,4-imino-2,3-O-isopropylidene-D-ribitol;
7. Deprotecting the compound from step 6 under acidic conditions to provide the target compound.

The azasugar and analogs thereof can be obtained by known methods such as described in PCT WO 99/19338 to Furneaux et al.

In addition, compounds wherein A is represented by formula 1 can be prepared as follows:

1'. Reacting 2-chloro-4-methyl-3-nitropyridine with methylene to give the corresponding methoxide compound;
2'. Condensing the methyl group with dimethylformamide dimethyl acetal to give the corresponding enamine;
3'. Hydrogenating the compound from step 3;
4'. Protecting the NH group with a blocking compound; and
5'. Hydrogenating the compound from step 4 to provide the corresponding bromo compound; and continuing with steps 5–7 discussed above.

Compounds wherein A is presented by formula 2, can be prepared as follows:

1. Nitrating 3-methyl-5-nitrophenol to provide the corresponding dinitrophenol compound;
2. Condensing the methyl group of this compound from step 1 with dimethylformaldehyde dimethyl acetal;
3. Hydrogenating the compound from step 2 to cyclize it;
4. Protecting the hydrogen groups with blocking groups;
5. Bromonating the compound from step 4 to provide the corresponding bromo compound;
6. Reacting the compound from step 5 with an alkyl lithium compound to replace the bromo group with a lithium group forming an anion of the bromo compound from step 5;
7. Condensing the compound from step 6 with 5-O-t-butyldimethyl silyl-1, N-dehydro-1,4-dideoxy 1,4-imino -2,3,-O-isopropylidene-D-ribitol.
8. Deprotecting the compound from 7 under acidic conditions to provide the target compound.

Compound wherein A is represented by formula 3 can be prepared as follows:

1. Condensing 2-aminoacetaldehyde and ethyl-3-cyano-2-oxopropanate to form a pyrrole;
2. Protecting the hydrogen with a blocking compound;
3. Hydrolysing the compound from step 2 to form the corresponding acid compound;
4. Converting the acid compound from step 3 to the corresponding acid halide;
5. Reacting the compound from step 4 with an alkyl lithium compound to form the corresponding ketone;
6. Reacting the ketone from step 5 with lithium diisopropylamide (LDA).
7. Reacting the product from step 6 with TMSCl to provide the corresponding enolate;
8. Reducing the compound from step 7 to provide to corresponding amino-methyl compound.
9. Reacting the compound from step 8 with Bromine to cyclize it;
10. Converting the compound from step 9 to a ketal;
11. Reacting the compound from step 1 with chloromethyl benzyl ether (BOMCl);
12. brominating the compound from step 11;
13. Reacting the compound from step 12 with an alkyl lithium compound to replace the bromo groups with a lithium group, or forming a Grignard of the bromo compound from step 12;
14. Condensing to compound from step 13 with 5-O-t butyl dimethyl-silyl-1,N-dehydro-1,4-dideoxy 1,4-imino-2,3-O-isopropylidene-D-ribitol; and
15. Deprotecting the compound from step 14 under acidic conditions to provide the target compound.

Still other objects and advantages of the present invention will become readily apparent by those skilled in the art from the following detailed description, wherein it is shown and described preferred embodiments of the invention, simply by illustration of the best mode contemplated of carrying out the invention. As will be realized the invention is capable of other and different embodiments, and it's several details are capable of modifications in various obvious respects, without departing from the invention. Accordingly, the description is to be regarded as illustrative in nature and not as restrictive.

BEST AND VARIOUS MODES FOR CARRYING OUT INVENTION

The present invention relates to compounds represented by the formula:

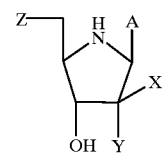

I wherein A is selected from the group consisting of

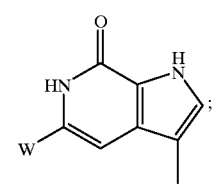

1

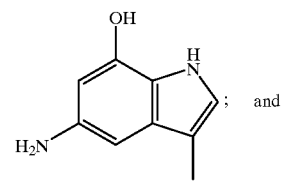

2

; and

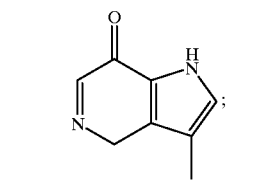

3

W is H or $NH_2$;

each X, Y and Z is individually selected from the group consisting of H, OH and halogen provided that at least one of X and Y is H; tautomers and pharmaceutically acceptable salts thereof.

Suitable halogen groups include chlorine, bromine and fluorine and preferably fluorine.

Preferred compounds of the present invention are represented by the formula:

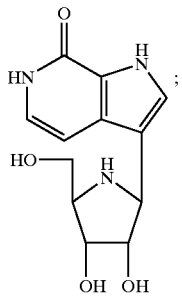

II tautomers and pharmaceutically acceptable salt thereof.

Suitable salts include acid additional salts. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluroacetic and benzenesulfonic acids.

Compounds of the present invention wherein A is represented by formula 1, can be prepared as shown below in Scheme 1. In this method, the key starting material 9 can be prepared from 7 which is known via a multi-step sequence (see Rose, J. D., Secrist, III, J. A., Montgomery, J. A., *J. Nucleotides and Nucleosides*, in press) in which commercially available 2-chloro-3-nitropyridine was reacted with sodium methoxide to give the corresponding 2-methoxy compound 1.

Reduction of the nitro group with Raney-Ni or 5% Pd-C with $H_2$ gives 3-amino-2-methoxypyridine 2 which is then condensed with the chlorosulfonium chloride intermediate 3 to give 4. Rearrangement of 4 under basic conditions gives the ortho-amino substituted intermediate 5. Treatment of 5 with concentrated HCl effects both cyclization and deprotection of the methoxy group to the corresponding carbonyl 6. Reaction of 6 with Raney-Ni gives known 7. Conversion of 7 to the corresponding 6-chloro compound 8 was accomplished with POCl3. Production of the NH group with benzyloxymethyl chloride gave 9. Replacement of the chloro with methoxy was accomplished with methoxide to afford 10 followed by bromination (Br2/CHCl3) to give 11.

Condensation of the lithio anion of 11 (prepared by reaction of 11 with n-butyl lithium under standard conditions) with 5-O-t-butyldimethylsilyl-1, N-dehydro-1,4-dideoxyl,4-imino-2,3-O-isopropylidene-D-ribitol 13 (see Fleet, G. W. J., Son, J. C., Tetrahedron, 1988, 44, 2637–2647 and Furneaux, R. H., Limberg, G., Tyler, P. C., Tetrahedron, 1997, 53, 2915–2930) gives 14. Alternatively, the Grignard of 11 can also be prepared and added to imine 13 (see Horenstein, B. A., Zabinski, R. I., Schramm, V. L., Tetrahedron Lett., 1993, 34, 7213–7216). Final deprotection under acidic conditions with HCl affords 15. Methods of synthesizing the azasugar and the claimed analogs are described in PCT WO 9919338 by Furneaux, R. H., Tyler, P. C., and Schramm, V. L.

Alternatively, the key intermediate 11 is prepared according to Scheme 2. Reaction of methoxide with 2-chloro-4-methyl-3-nitropyridine (commercially available) gives the corresponding methoxy compound 16. Condensation of the methyl group with dimethylformamide dimethyl acetal gives enamine 17. Treatment of 17 with H2 in the presence of 5% Pd-C (15 psig) gives 18. Protection of the NH group (NaH/chloromethyl benzyl ether) gives 19 which is brominated (Br2/CHCl3) to give 11 (BioCryst has prepared 11 using this route as described in Scheme 2).

Compounds of the present invention wherein A is represented by formula 2, may be prepared as described in Scheme 3 in which 3-methyl-5-nitrophenol (see Gu. S., Huanwang, J., Wu, J., Liang, Y., Synth. Commun., 1997\, 27 (16), 2793–2797) is nitrated to give 21. Condensation of the methyl group with dimethylformamide dimethyl acetal gives 22 which is cyclized to 23 by hydrogenation. Exhaustive protection with BOMCl/NaH gives 24 which can be brominated to give 25. Condensation of the lithio anion of 26 (prepared by reaction of 25 with n-butyl lithium under standard conditions) with 5-O-t-butyldimethylsilyl-1,N-dehydro-1,4-dideoxyl 1,4-imino-2,3-O-isopropylidene-D-ribitol 13 (see Fleet, G. W. J., Son, J. C., Tetrahedron, 1988, 44, 2637–2647 and Furneaux, R. H., Limberg, G., Tyler, P. C., Tetrahedron 1997, 53, 2915–2930) gives 27. Alternatively, the Grignard of 25 can also be prepared and added to imine 13 (also see Horenstein, B. A., Zabinski, R. I., Schramm, V. L., Tetrahedron Lett., 1993, 34, 7213–7216). Final deprotection under acidic conditions with HCl to affords 28. In a similar manner, the pyridine analog of 20 may also be used to afford 29.

Compounds of the present invention wherein A represented by formula 3 may be prepared as described in Scheme 4. Knorr condensation of 2-aminoacetaldehyde and ethyl 3-cyano-2-oxopropanoate affords pyrrole 30. Protection with BOMCl give 31. Mild base hydrolysis of the ester to the corresponding acid affords 32. Conversion of the acid to the chloride (SOCl2) followed by reaction with methyl lithium gives ketone 33. Reaction to the ketone with LDA then TMSCl gives the kinetic trapped enolate 34. Reduction of the nitrile with LAH gives the aminomethyl compound 35. Reaction with Br2 gives ketone 33. Reaction of the ketone with LDA then TMSCl gives the kinetic trapped enolate 34. Reduction of the nitrile with LAH gives the aminomethyl compound 35. Reaction with Br2 gives the cyclized product 36. Production of the ketone as the ketal followed by N protection with BOMCl gives 37. Bromination (Br2/CCl4) gives 38.Condensation of the lithio anion of 38 (prepared by reaction of 38 with n-butyl lithium under standard conditions) with 5-O-t-butyldimethylsyl-1,N-dehydro-1,4-dideoxyl,4-imino-2,3-O-isopropylidene-D-ribitol 13 (see Fleet, G. W. J., Son, J. C., Tetrahedron, 1988, 44, 2637–2647 and Furneaux, R. H., Limberg, G., Tyler, P. C., Tetrahedron 1997, 53, 2915–2930) gives 39. Alternatively, the Grignard of 38 can also be prepared and added to imine 13. Final deprotection under acidic conditions with HCl to afford 40.

LDA=lithium diisopropylamide
TMSCl=trimethylsilyl chloride
LAH=lithium aluminum hydride Scheme 1

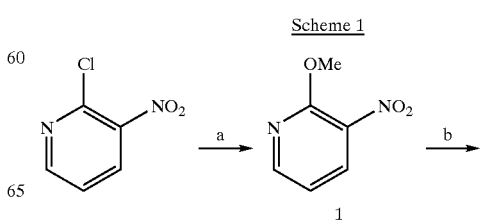

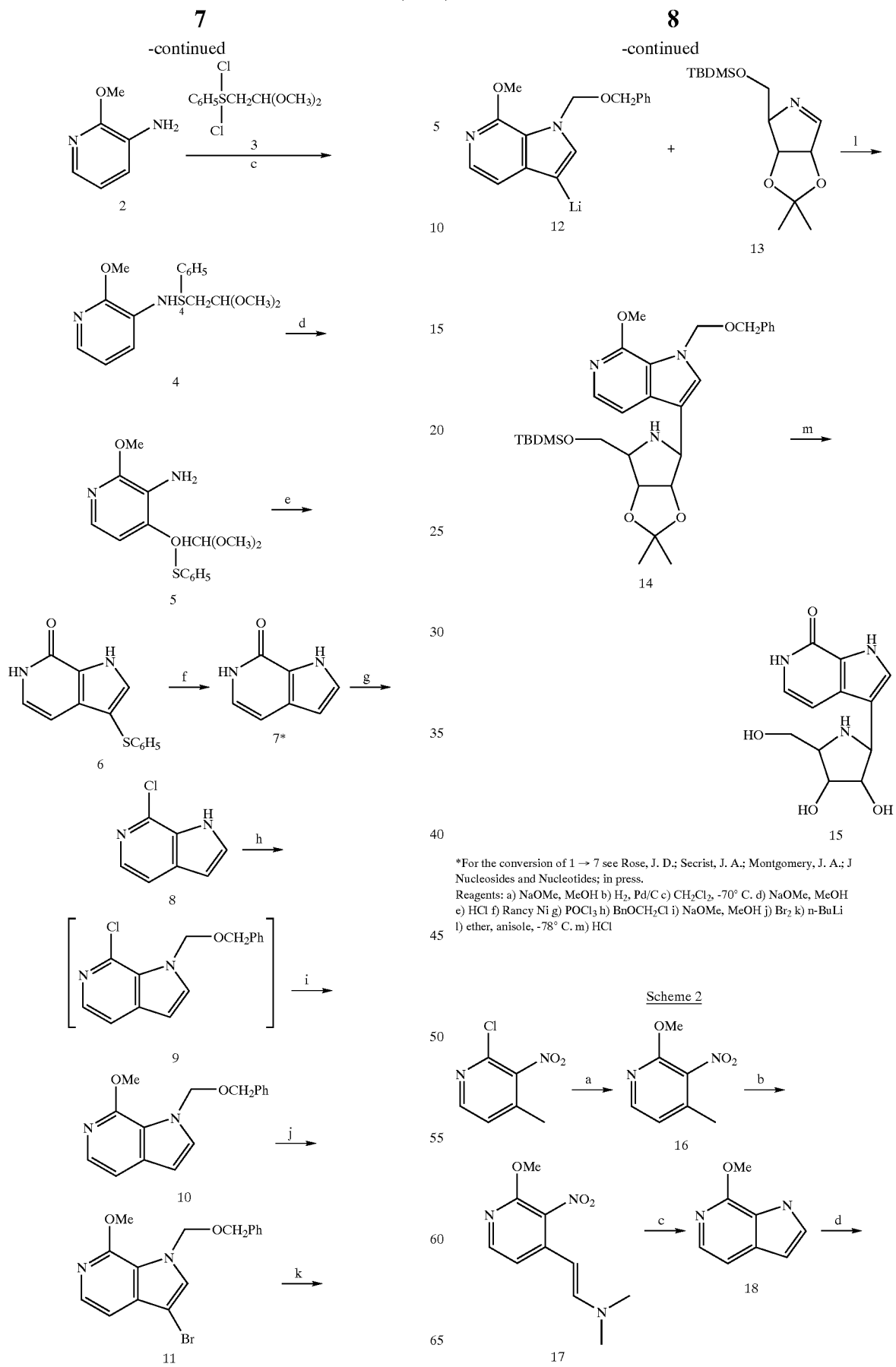

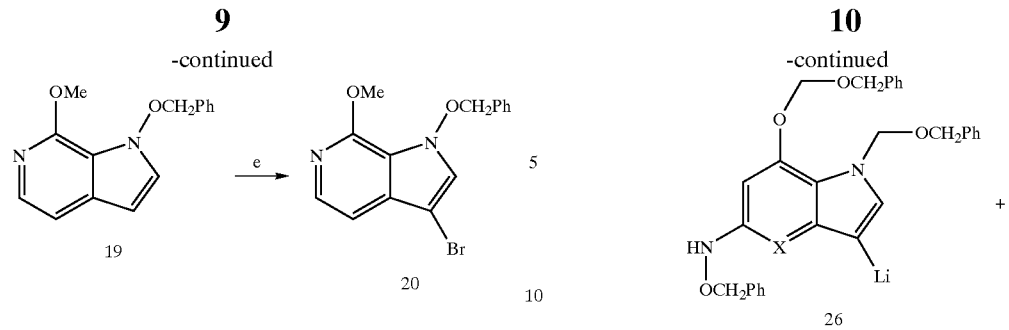
Reagents: a) NaOMe, MeOH b) DMF•(OMe)$_2$, MeOH c) H$_2$, Pd/C d) NaH, ClCH$_2$OCH$_2$Ph e) Br$_2$, CCl$_4$, THF
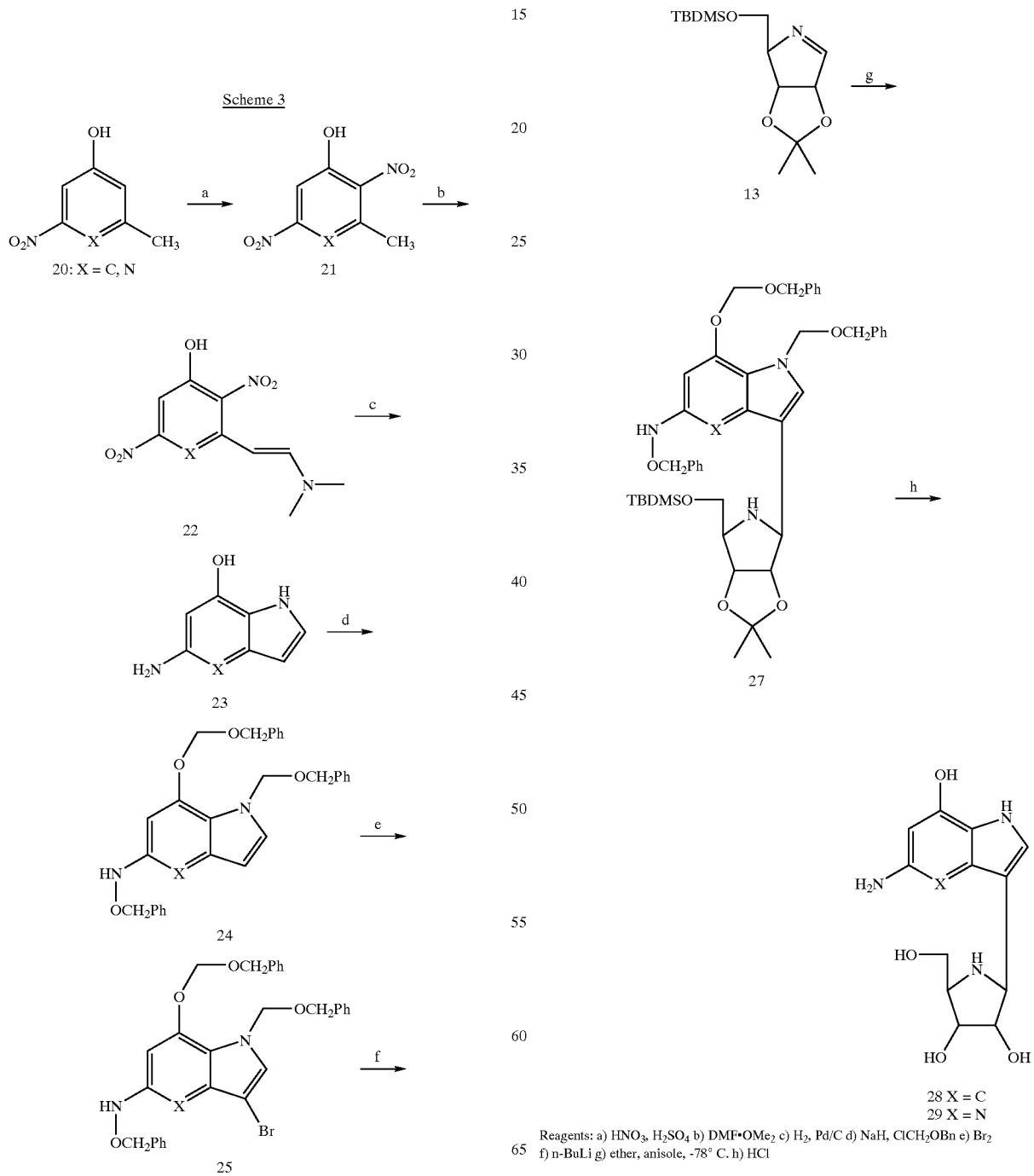
Reagents: a) HNO$_3$, H$_2$SO$_4$ b) DMF•OMe$_2$ c) H$_2$, Pd/C d) NaH, ClCH$_2$OBn e) Br$_2$ f) n-BuLi g) ether, anisole, -78° C. h) HCl

Scheme 4

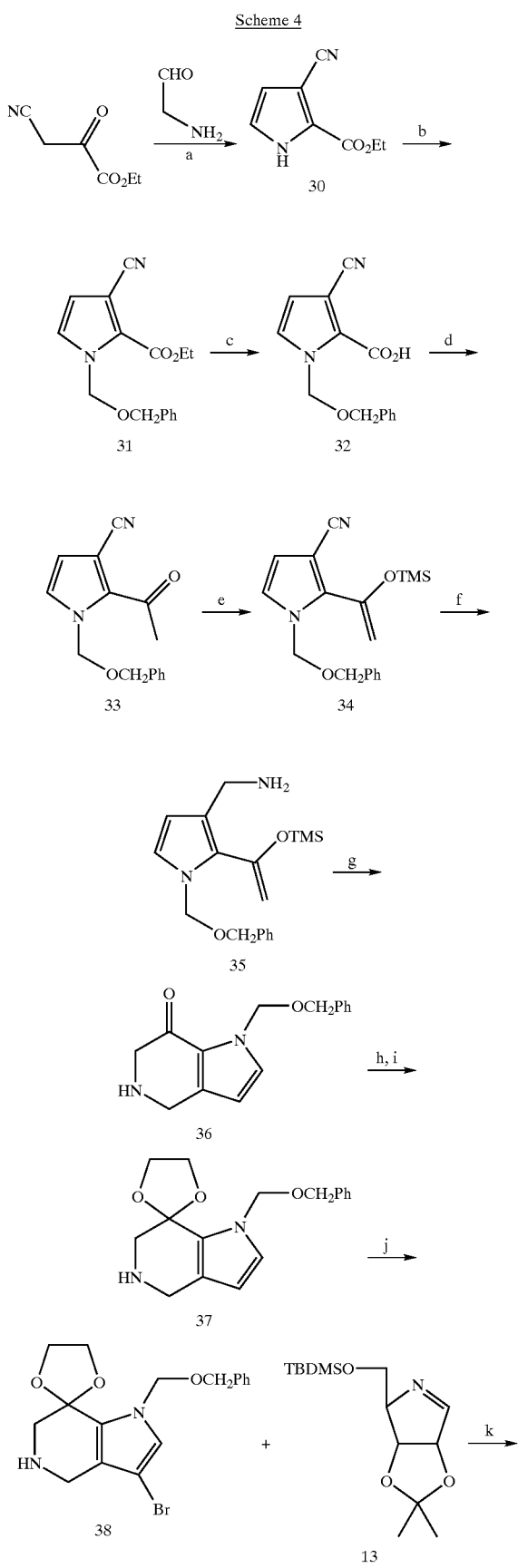

Reagents: a) H+ b) NaH, ClCH2OBn c) mild base, d) SOCl2, than CH3Li e) LDA, then TMSCl f) LiAlH4 g) Br2 h) HOCH2CH2OH, acid i) NaH, ClCH2OBn j) Br2 k) ether, anisole, -78° C. l) HCl m) oxidation Pursuant to the present invention, the compounds of the present invention, tautomers and/or their acid addition salts, can be used alone or in appropriate association, and also may be used in combination with pharmaceutically acceptable carriers and other pharmaceutically active compounds such as cancer treatment drugs. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this invention can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5–95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238–250 (1982) and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an animal are available, and, although more than one route can be used to administer a particular compound, a particular route can provide a more immediate and more effective reaction than another route.

Compounds of the present invention can be used to inhibit PNP and to prevent T-cell proliferation. Accordingly, such can be used for T-cell proliferation disorders. For example, compounds and compositions of the present invention can be administered to treat a number of cancers, including leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The method of the present invention is applicable in the treatment of brain, colon, renal and mammary tumors, and preferably colon, brain and mammary tumors. The method of the present invention can be practiced on mammals, particularly humans.

The dose administered to an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer, without unmanageable side effects.

The total amount of the compound of the present invention administered in a typical treatment is preferably between about 60 mg/kg and about 2000 mg/kg of body weight for mice, and between about 5 mg/kg and about 100 mg/kg of body weight, and more preferably between 5 mg/kg and about 20 mg/kg of body weight for humans. This total amount is typically, but not necessarily, administered as a series of smaller doses over a period of from about one day to about 24 months, and preferably over a period of 28 days to about 12 months.

The size of the dose also will be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

The method of the present invention comprises further administering of a chemotherapeutic agent in combination with the compounds of the present invention. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, azaserine, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL (paclitaxel), taxotere, teniposide, vincristine, vinorelbine, mithramycin, idarubicin, MITHRACIN™ (plicamycin), and deoxycoformycin.

An example of a hormonal chemotherapeutic agent includes tamoxifen. Examples of the aforesaid miscellaneous chemotherapeutic agents include mitotane, mitoxantrone, vinblastine, and levamisole.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. Compound represented by the formula:

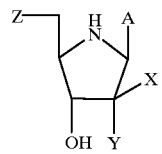

I wherein A is selected from the group consisting of

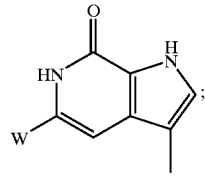

1

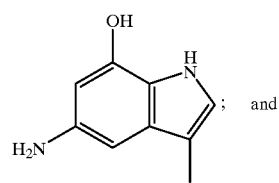

2

; and

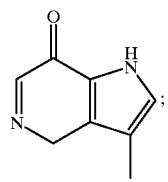

3

W is $NH_2$ or H; each X, Y and Z is independently selected from the group consisting of H, OH and halogen provided that at least one of X and Y is H; W is H or NH2; a tautomer or a pharmaceutically acceptable salt thereof.

2. A pharmaceutical composition comprising at least one compound of claim 1 and a pharmaceutically acceptable carrier.

3. A method for suppressing purine nucleoside phosphorylase in a patient by administering to the patient in need thereof at least one compound of claim 1 in an amount sufficient to suppress purine nucleoside phosphorylase.

4. A method of inhibiting T-cell proliferation in a patient which comprises administering to the patient in need thereof at least one compound of claim 1 in an amount sufficient for inhibiting T-cell proliferation.

5. Compound of claim 1 represented by the formula

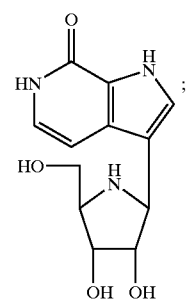

II a tautomer, or a pharmaceutically acceptable salt thereof.

* * * * *